United States Patent [19]

Charm et al.

[11] Patent Number: 5,728,542
[45] Date of Patent: *Mar. 17, 1998

[54] DISPOSABLE TEST KIT APPARATUS AND METHOD FOR BACTERIA

[75] Inventors: Stanley E. Charm, Boston; Max Gandman, Malden; Eliezer Zomer, Newton, all of Mass.

[73] Assignee: Charm Sciences, Inc., Malden, Mass.

[*] Notice: The term of this patent shall not extend beyond the expiration date of Pat. No. 5,605,812.

[21] Appl. No.: 614,813

[22] Filed: Mar. 8, 1996

Related U.S. Application Data

[63] Continuation-in-part of Ser. No. 446,039, May 19, 1995, Pat. No. 5,605,812.
[51] Int. Cl.$^6$ .............................. C12Q 1/06; C12Q 1/10; A61L 2/16
[52] U.S. Cl. .................. 435/38; 435/7.37; 435/39; 422/28
[58] Field of Search .................. 435/38, 29, 30, 435/34, 39, 7.37, 810, 975; 422/28

[56] References Cited

U.S. PATENT DOCUMENTS

| | | | |
|---|---|---|---|
| 5,393,662 | 2/1995 | Roth et al. | 435/38 |
| 5,411,867 | 5/1995 | Chang et al. | 435/38 |
| 5,518,892 | 5/1996 | Naqui et al. | 435/29 |
| 5,598,919 | 2/1997 | Taylor | 206/5.1 |
| 5,605,812 | 2/1997 | Zomer | 435/38 |

*Primary Examiner*—Marian C. Knode
*Assistant Examiner*—Donna C. Wortman
*Attorney, Agent, or Firm*—Richard P. Crowley

[57] ABSTRACT

A safe, disposable test kit apparatus for the detection of pathogens in a test sample, such as coliform bacteria and *E. coli*. The apparatus comprises a transparent plastic bag divided into a sample compartment to receive a test sample such as water and a media compartment having a powdered growth medium with an indicator for the pathogens. The test kit apparatus includes a sanitizer compound or composition in a separate compartment to be introduced into the sample and media compartment after incubation and reading of the test results to provide for the total deactivation of the pathogen grown on the media after incubation thereby permitting the safe disposal of the plastic bag with the ingredients therein.

39 Claims, 6 Drawing Sheets

TEST METHOD

1. Place water sample (16) in sample compartment (20) of bag (12).

2. Seal sample compartment (20).

3. Rupture heat seal (34) and mix sample (16) with neutralizer (24).

4. Mix neutralized water sample with media (28); press bag flat.

5. Incubate to culture media with sample.

6. Detect coliform bacteria by color change.

7. Detect *E. coli* by ultraviolet light.

8. Mix sanitizer (32) with cultured media and sample.

9. Discard sanitized bag.

FIG. 7

DISPOSABLE TEST KIT APPARATUS AND METHOD FOR BACTERIA

REFERENCE TO PRIOR APPLICATION

This application is a continuation-in-part application of U.S. patent application Ser. No. 08/446,039, filed May 19, 1995 now U.S. Pat. No. 5,605,812, issued Feb. 25, 1997, which application is incorporated by reference herein.

The parent application is directed to a test method and test kit for the determination of bacteria, particularly for the qualitative and quantitative determination of total coliform bacteria and E. coli in a test sample. The method comprises combining in a transparent, flexible, plastic container a water sample to be tested for a total coliform bacteria and E. coli with a powdered test composition. The powdered test composition comprises a growth nutrient medium for the coliform bacteria and a first agent therein which is cleaved by an enzyme in the coliform bacteria to produce a color in the resulting media broth, such as a blue-green color, and to indicate by the presence of the color, the presence in the test sample of coliform bacteria. The test composition also includes a second, fluorescent agent, which is also cleaved by an enzyme in the E. coli bacteria of the test sample, to indicate by the presence of a fluorescent color the presence of E. coli bacteria in the test sample upon exposure to ultraviolet light. The test method includes observing the color change or absence thereof and observing fluorometrically the fluorescent color change, or absence thereof, to determine qualitatively the presence of total coliform bacteria and/or E. coli bacteria in the test sample. In one embodiment, the test method and test kit provide a water soluble, powdered gelling agent in the test composition, and which gelling agent reacts in situ in the presence of the water in the test sample to form a transparent, semisolid medium prior to incubation of the test sample, and typically, within about two hours. The formation of the gel restricts the mobility of the coliform bacteria and E. coli during the subsequent incubation period and provides for the growth of separate colonies of the coliform bacteria in the gel and separate colonies of the E. coli so that the total coliform bacteria, as well as the E. coli, may be quantitatively measured.

The parent application also describes a test kit for the determination of coliform bacteria and E. coli which comprises a flexible, transparent, plastic bag as a container for the test sample, and which test sample comprises water or a sample having a water content. In one embodiment, the test container comprises a sealable, flexible, transparent, plastic bag, for example, sealed by a wire plastic strip, and also includes at least two chambers separated by a dividing means, the first chamber for the introduction of the test sample, and a separate chamber to contain the powdered test composition, so that by removal of the dividing means by the user, the test sample in the first chamber and the powdered composition in the separate chamber may be admixed by the user after sealing of the plastic bag. In the method of operation, the plastic bag after being kneaded for mixing of the sample with the powdered test composition is pressed into a flat condition, and then incubated to form a gel, and then observed to detect qualitatively the presence of the coliform bacteria and/or E. coli under ultraviolet light, and then also, the total coliform bacteria or the E. coli may be quantitatively determined in the cultured media in the flat plastic bag.

BACKGROUND OF THE INVENTION

The test kit and method of the parent application provide for a method of effective and easy determination of total coliform bacteria and E. coli in a test sample, particularly a large volume water sample, such as 10 ml to 500 ml, and is subject to use in field conditions because it is quite simple and provides for the simplified collection and detection of the bacteria. As set forth in the parent application, after carrying out of the test, the plastic bag with its contents, that is, the cultured media, the test sample and the coliform bacteria and E. coli grown therein during the incubation phase, may be easily disposed of as trash after treatment, such as the employment of boiling water for ten minutes or the employment of autoclaving the plastic bag before disposal. The standard EPA instruction to discard a used microbiological test media is by employing an autoclave at 121° C. However, autoclaves are not available in all laboratories and are not available in the general retail or consumer market. Any test kit apparatus which employs a disposable, used microbiological media containing grown bacteria which is used for the detection of potential pathogens, for example, E. coli or salmonella, requires a safe disposal of the test kit apparatus.

It is therefore desirable to provide for safe and effective disposal of a used microbiological test media in a test container, such as a plastic bag, particularly where the test kit apparatus is employed by unsophisticated laboratory personnel and in non-laboratory conditions, and which disposal means and method provide for a safe, easy, simplified disposal of the potentially pathologically dangerous culture media and the grown bacteria therein.

SUMMARY OF THE INVENTION

The present invention relates to a safe, disposable, test kit apparatus and method for disposing of used microbiological test media and microorganisms, including pathogen organisms, grown thereon. In particular, the invention relates to an effective, simple, safe, easy means of disposing of plastic bag test kits containing used media and bacteria.

The invention relates to a safe, disposable test kit apparatus designed for the detection of pathogens, such as coliform bacteria and E. coli, and other pathogens in a test sample of which the test kit apparatus after use may be easily disposed in a bacteriological, safe manner. The test kit apparatus comprises a transparent, flexible, plastic, multi-compartment packaging means, such as a bag of defined internal volume to receive a test sample, such as a water sample of 10 ml to 500 ml, and which comprises a plurality of at least first, second and third separate, adjacent, sealed compartments in the packaging means.

The packaging means includes a first compartment having an open end to receive a test sample and means to seal the open end of the first compartment after receipt of the test sample. The package may also include seal or divider means to seal or divide each of the compartments from each other and to permit a user to remove the seal or divider means for the sequential mixing of ingredients in the respective compartments. The packaging means includes a first sample compartment adapted to receive therein a defined volume of a liquid test sample, such as a water sample to be tested for E. coli and total coliform bacteria, as an illustrative example. The packaging means includes a second media-type compartment containing a culture growth medium and a selected bacteria indicator, and particularly comprises a powdered test medium which includes a test medium for the growth of the bacteria and agents which change color to detect for example coliform bacteria and a fluorescent agent to detect E. coli bacteria under ultraviolet light.

The packaging means includes a third adjacent or separate sanitizer compartment which contains a sanitizer, which sanitizer is selected to destroy and render inactive any of the grown microorganisms in the cultured growth media within the packaging means, such as within the plastic bag, after incubation and detection, either qualitatively or quantitatively, of the microorganisms.

In the sanitizer test kit apparatus, the test sample is introduced into the first compartment and then the compartment sealed. The test sample is then admixed with the culture medium in the second compartment after the removal of the seal means between the first and second compartments, and is admixture of the test sample and medium is then incubated, typically with the plastic bag pressed in a flat condition, where the culture medium contains a gelling agent. The incubated admixture is then read to detect qualitatively and/or quantitatively the pathogens in the test sample. Prior to disposal, and after incubation and reading of the test sample, the used, incubated culture media with the test sample and the grown pathogens thereon is subsequently admixed with the sanitizer of the third compartment by the removal of the means between the second and third compartments or the separate introduction of the sanitizer by any means wherein the presence and admixture of the sanitizer destroys or renders inactive the growth pathogens and thereby permits the safe disposal of the entire packaging means or sealed plastic bag into the trash. The test kit and method are particularly adapted for test kits and apparatus used in the field and used by unsophisticated laboratory personnel or by consumers, and thus avoids the necessity of heat treating the sealed plastic bag or autoclaving the bag prior to removal of the dangerous pathogen components therein.

The sanitizing compounds employed may comprise a wide variety of chemical antibacterial or antipathogenic agents, either alone or in admixtures, such as sanitizers or oxidizers which are well known and routinely used in hospitals, the food industry and consumer markets for the control of microorganisms. The user of the test kit can provide for the destruction of the known pathogens within the plastic bag at the end of the test, and thus permit the safe disposal of the test kit apparatus. The sanitizing agent should be selected to kill all live pathogens, such as the total coliform bacteria and $E.$ $coli$, in the particular test method employed, so that the resulting test container can then be safely discarded.

Sanitizing compounds employed may vary and include oxidizing-type chemicals, such as the hypohalides, or more particularly sodium hypochloride, and may include organic acids, such as peracetic acid; peroxides, including hydrogen peroxide and perborate oxides or halogens like iodine and iodide compounds; and also aldehydes, such as formaldehyde and glutaraldehyde. Other sanitizers which are detergent-type sanitizers would include, but are not limited to, quaternary ammonium compounds or other sanitizers which have detergent or surface action effects, such as more particularly benzalkonium halides, such as benzalkonium chlorides, as well alkyl benzyl quaternary ammonium bromides or chromides, more particularly as dimethylalkyl quaternary ammonium chlorides, or fatty acid pyridinium halides like cetyl pyridinium chloride or bromide, as well as alkali metal lauryl sulfates, such as sodium lauryl sulfate. The sanitizing agents may be used alone or in combination. For example, an effective sanitizing agent may include an oxidizing-type chemical together with a quaternary ammonium-type chemical. Typically, the sanitizing agent is employed in liquid form in the third compartment or as a separate capsule alone or in the plastic bag compartment. The concentration of the sanitizer compound should be sufficient to provide for the total destruction of the pathogenic organisms in the cultured growth media. The concentration of the sanitizing agent may vary; however, generally the concentration should be at least as great as, or typically more than sufficient to provide for the destruction of all the suspected pathogenic organisms.

Additionally, but preferably, it is also desirable to employ an indicating agent in combination with the sanitizer, such as an indicating dye, for example, black or other brightly visible color, water soluble dye, such as a food dye, in combination with the sanitizer, so that when the sanitizer is released for example from the third compartment or separately introduced into the cultured media and pathogens, the dye may act as an indicator to establish mixing of the cultured media and pathogens with the sanitizer to ensure total mixture and destruction of the grown pathogens. A black food dye is one preferred dye indicator selected for use with the sanitizer, since a black color would prevent children from contacting or drinking the contents of the bag or vial. Further, other colors like light yellow, red or blue which are indicators of the test results preferably should not be used, since these colors may encourage children to drink the contents if they mistaken it as to a juice-type product. Thus, the dye indicator selected should be child safe, and particularly where consumer use is intended of the test kit apparatus, to indicate that the sanitizer has been totally mixed with the grown culture media and pathogens.

The sanitizing agent may be incorporated into the test kit apparatus in a variety of ways. In one embodiment wherein a compartment is employed in the flexible plastic bag and the compartment is then sequentially opened to first provide for a mixing of the test sample with the culture medium, and then after incubation, mixing of the culture medium with the grown pathogen with the sanitizing agent. There are also other techniques employed to introduce the sanitizing agent into the cultured medium and grown pathogens. For example, a separate, burstable capsule containing the sanitizing agent may be employed. The burstable capsule may, for example, be a pressure-sensitive capsule, such as one burst by hand pressure, and placed within the bag either before or after incubation, and sufficient so that the capsule may not be activated or burst during the incubation period, or in fact, the pressure-sensitive capsule may be introduced into the bag after incubation, though this is not a preferred method, and then the pressure-sensitive capsule burst after reading of the test results, thus to provide for the destruction of the pathogens within the bag.

In another embodiment, a pressure-sensitive pocket or plug may be built into the flexible plastic bag of the test kit apparatus as an integral part thereof, and after incubation and reading of the test results, pressure applied by the user to force the sanitizing agent in the pressure-sensitive pocket, alone or together with the color indicator, into the incubated media and pathogens. In a further embodiment of the invention, a time released means may be employed that is activated by the addition of water. For example, the plastic bag may have an elongated neck or plug or other device in the plastic bag plugged with a mixture of a water-soluble material, such as starch or amylase or a solid lipid and lipase, so that on contact with the water test sample, the enzyme is then activated, which slowly digests the plug over a selected time period greater than the incubation time period.

The length of the plug and the rate of digestion is precalculated in use, so that at the end of the incubation period, for example, 24 hours at 35° C. or 36, 48 or 72 hours as desired, the plug would be burst exposing the sanitizer in the compartment to the cultured media and the grown pathogens. Thus, the sanitizing agent may be employed in a precalculated, time release manner activated by the test sample or by incubation temperature, so as to prevent for example the inadvertent nonuse of the sanitizer by a user, such as a consumer user, so that the flexible bag with the cultured media and the grown pathogens would be automatically decontaminated and safe to dispose regardless of the failure to act of the user.

It is often desirable as set forth in the parent application, particularly with water test samples, that the water sample be neutralized prior to admixture with a medium, so as to reduce the effect of halogens, such as chloride, in the water test samples, for example by the use of a thiosulfate prior to admixture of the powdered test medium, such as the powdered, gellable test medium as described in the parent application. Thus, the packaging means may include an intermediate, separate, sealed compartment containing a neutralizing agent, such as a water solution of a thiosulfate, to neutralize chlorine as recommended by the EPA in the water test sample prior to admixing the neutralized water sample with the powdered test medium in the second compartment.

The packaging means employed as set forth more particularly in the parent application and as incorporated herein, would include and comprise a flexible plastic bag having an open one end and means to seal the open one end of the bag. The plastic bag is typically transparent to permit the reading of the test results in the bag and is flexible so that the bag may be pressed into a flattened condition for incubation, where gelling agents are used. The bag would also contain printed on a portion thereof containing the medium and the test sample a plurality of grids or squares, so that the grown pathogens therein, for example, the total coliform bacteria and/or *E. coli* may be easily quantitatively read by a user. Generally, the plastic bag would have a means to seal the open mouth of the bag after the introduction of the test sample therein. For example, it may contain a plastic wire strip extending around and outwardly from the mouth, so that the user may merely twirl the open mouth of the bag around and use the wire strip to seal completely the open mouth of the bag after the introduction of the test sample.

The flexible plastic bag typically would have at least two compartments which may be separated by a dividing means. For example, the dividing means may include a clip means, that is, a plastic, tension-biased clip divider which is merely clipped to the outside of the bag to divide the bag into separate compartments, and wherein the clip is removed by a user in use to permit the sequential mixing of the ingredients in the compartments as required in the particular test. Thus, for example, in the parent application, a flexible plastic bag is employed with a disposable plastic divider clip to divide the bag into a medium compartment for a powdered, gellable test composition containing the growth medium, the agents and the gelling agents, and a separate compartment for the introduction of the water sample, with which the powdered test composition is to be admixed after sealing of the plastic bag.

Further, the plastic bag or the packaging means may be subdivided employing a seal line which extends across the plastic bag, so as to form and provide for separate, sealed compartments, which sealed compartments would have a seal line, such as a heat seal line, or an adhesive line extending across the length of the plastic bag to provide sealed compartments, which seal line to the sealed compartments may be easily ruptured by hand pressure of the user, so as to permit the sequential mixing of the ingredients in the compartments. The seal line may be formed by separate adhesives used or by merely the heat sealing together of the thermoplastic component film of the bag. Thus, the bag for example may comprise a bag which is peripherally heat sealed, having an open mouth with a wire sealing means to seal the open mouth, and a plurality of compartments, for example, at least two, but preferably three or four, divided by plastic clip means, or preferably by sealing lines extending across the plastic bag, which seal lines are burstable by a user.

The packaging may comprise a plastic disposable bag of a thermoplastic material which is readily heat sealed about its periphery to form heat sealing lines or which may be readily sealed by employing adhesives. However, it is recognized that the flexible plastic bag employed may comprise a multiple layer film bag, for example, employing a moisture impermeable layer so as to protect the medium and sanitizing agents to be stored in the bag to permit long time storage and employing inner and outer films over the other film which may be heat or adhesive sealable. Thus, the transparent, flexible plastic bag may be formed of a single thermoplastic film material or may be composed of a plurality of layers of different film materials as desired with typically a central oxygen barrier layer and an outer layer which is printable to permit the imprinting of the grid on the outside of at least a part of the plastic bag and also to permit instructions to be imprinted on the remaining part of the bag for the user.

The disposable, safe test kit apparatus comprises a packaging means, such as a flexible, transparent, plastic bag containing the media and containing means to receive the test sample, a separate compartment for the medium to mix with the test sample and containing means, such as a pressure burstable capsule, a time release plug or a separate compartment for the sanitizing agent, so as to provide for the subsequent sanitization of the grown pathogens after incubation and reading of the test results. The test apparatus may be easily employed in the field and by consumers and would merely comprise the flexible plastic bag containing the medium therein and the sanitizer and include incubation means, such as a simple oven, for incubation of the sealed plastic bag and an ultraviolet light as the fluorescent agent to determine *E. coli* or other pathogens where required.

Also, the test kit apparatus may comprise a plastic bag of two compartments and a separate, pressure releasable capsule containing the sanitizer agent separately applied or added to one of the compartments or may contain a plug within the bag. It is desirable to provide for a plastic bag composed of plastic materials which would withstand the incubation conditions and preferably having a plastic material which would withstand pasteurization conditions of, for example, 75° C. or more. Otherwise, incubation conditions would have to be adjusted to the tolerance of the plastic film that composes the plastic bag, such as for example, incubating at a lower temperature for a longer period of time. Preferably, however, the plastic bag would be made up of plastic polymeric components which will be pasteurized before use of the plastic bag with the components therein, such as for example, at 75° C. for 30 minutes or longer, so that the entire contents may be pasteurized after packaging. Otherwise, the plastic bag and its components, such as the powdered media, the sanitizing agent and the thiosulfate and other components used therein must be assembled and packaged under sterile conditions, which add to the cost and expense of the packaging means.

The invention will be described for purposes of illustration only in connection with certain preferred embodiments; however, it is recognized that various modifications, changes, additions and improvements may be made to the illustrated embodiments without departing from the spirit and the scope thereof.

DESCRIPTION OF THE EMBODIMENTS

Figure 1:
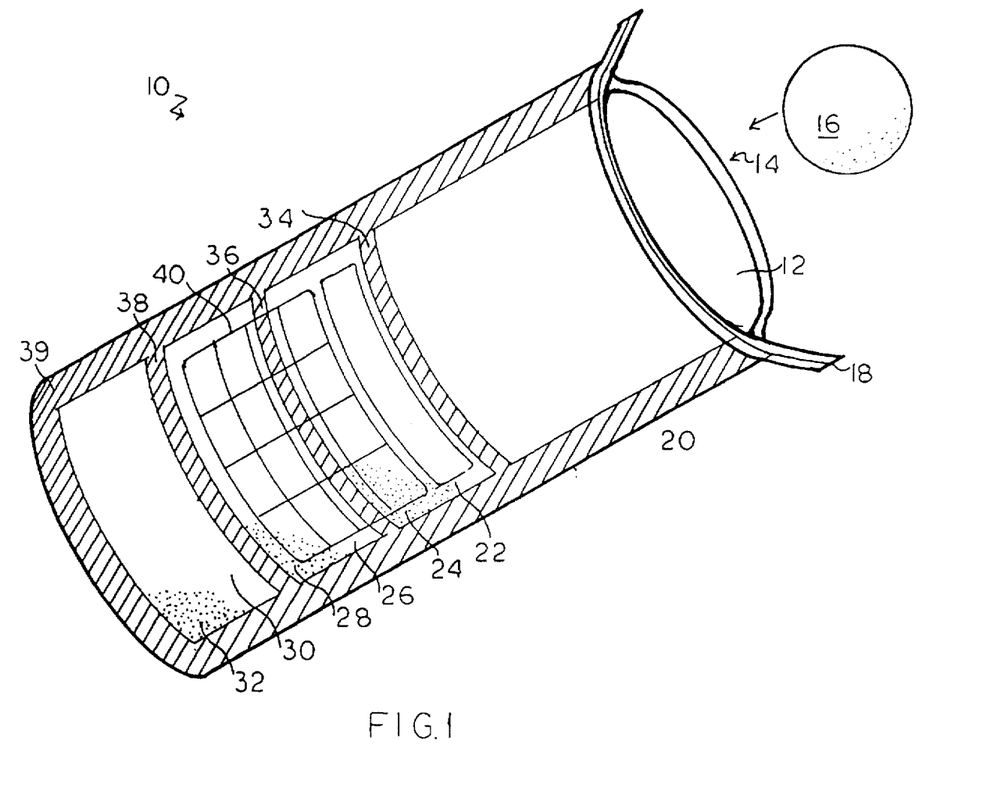
FIG. 1 is a perspective, illustrative view of one embodiment of the test kit apparatus of the invention.

In the drawings, FIG. 1 shows the test kit apparatus of the invention 10 in perspective, illustrative view. The media bag 12 has an open top 14 to permit the entry of a water sample 16. A closing wire 18 extends across the top of the open top 14 of the water sample collecting compartment 20. A rupturable heat seal 34 seals the water sample collecting compartment 20 from the sample neutralizer compartment 22, which has a neutralizer 24 sealed therein. A second rupturable heat seal 36 separates the sample neutralizer compartment 22 from the media compartment 26, which has the media and indicator 28 sealed therein. A final rupturable heat seal 38 separates the media compartment 26 from the sanitizer compartment 30, which has a sanitizer in powder form 32 sealed therein. An outer heat seal 39 extends around the three edges of the media bag 12 to seal all compartments of the media bag 12. An indicator grid 40 is printed on the top surface of the media and indicator compartment 26 to provide for reading of the mixed media sample 52. It is recognized that other printing or informative indicia may be printed on the media bag 12 as required and desired.

Figure 2:
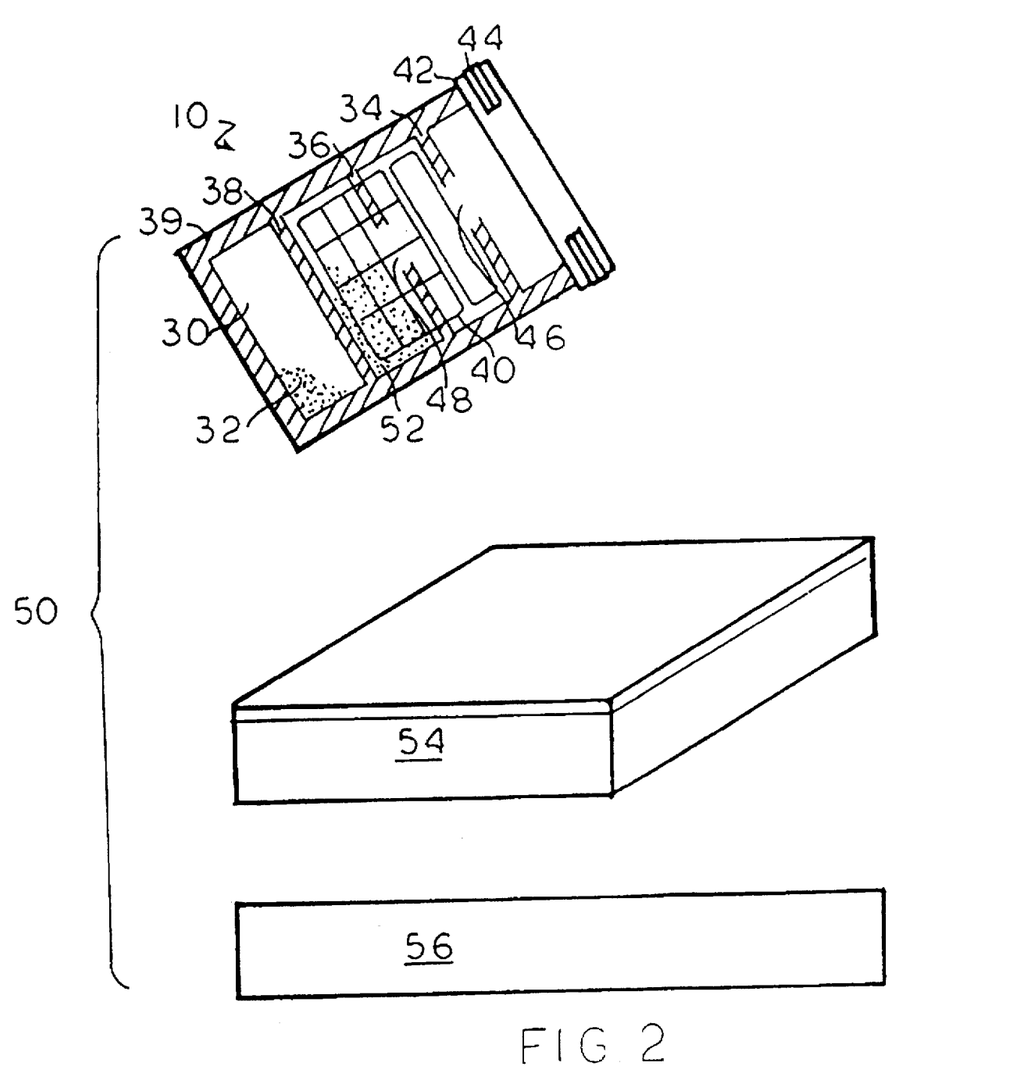
FIG. 2 is a schematic illustration of a test kit apparatus of the invention which includes the flexible plastic bag of FIG. 1.

FIG. 2 shows the test kit method of the invention 50, with the test kit of the invention 10 in a perspective illustrative position. The media bag 12 is shown with the open top 14 of FIG. 1 folded over and secured with the closing wire 18 of FIG. 1 to form a tie seal 44. The punctures of the puncturable heat seals 34 and 36 are shown as openings 46 and 48 respectively. Further, the mixed media sample 52, comprised of the water sample 16, neutralizer 24, and media/indicator 28 (as shown in FIG. 1) is shown in position under the indicia grid 40. The flattened media bag 12 is shown ready for placement in the incubator 54, with the ultraviolet light indicator 56 shown in a ready-to-use position after the test sample is incubated.

Figure 3:
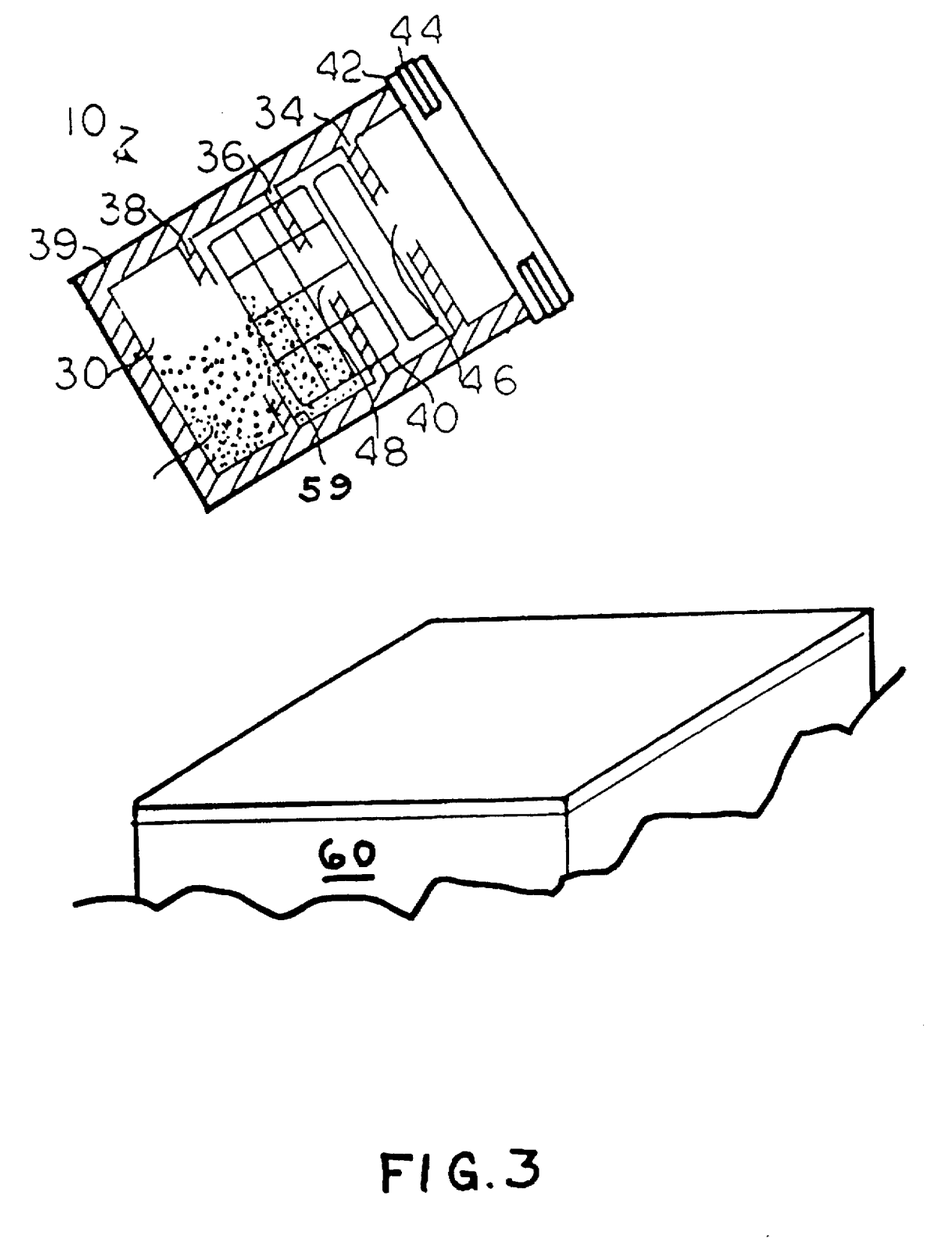
FIG. 3 is a perspective, illustrative view of the invention of FIG. 1 in a post-use, ready-to-dispose condition.

FIG. 3 shows the test kit of the invention 10 after use, with the rupturable heat seal 38 separating the media/indicator compartment 26 shown punctured and open 58 to allow for the sanitizer 32 to enter the media/indicator compartment 26 and sanitize the sample. The media bag 12, with the sanitized mixture 59 therein, is shown being disposed of in an appropriate waste receptacle 60.

Figure 4:
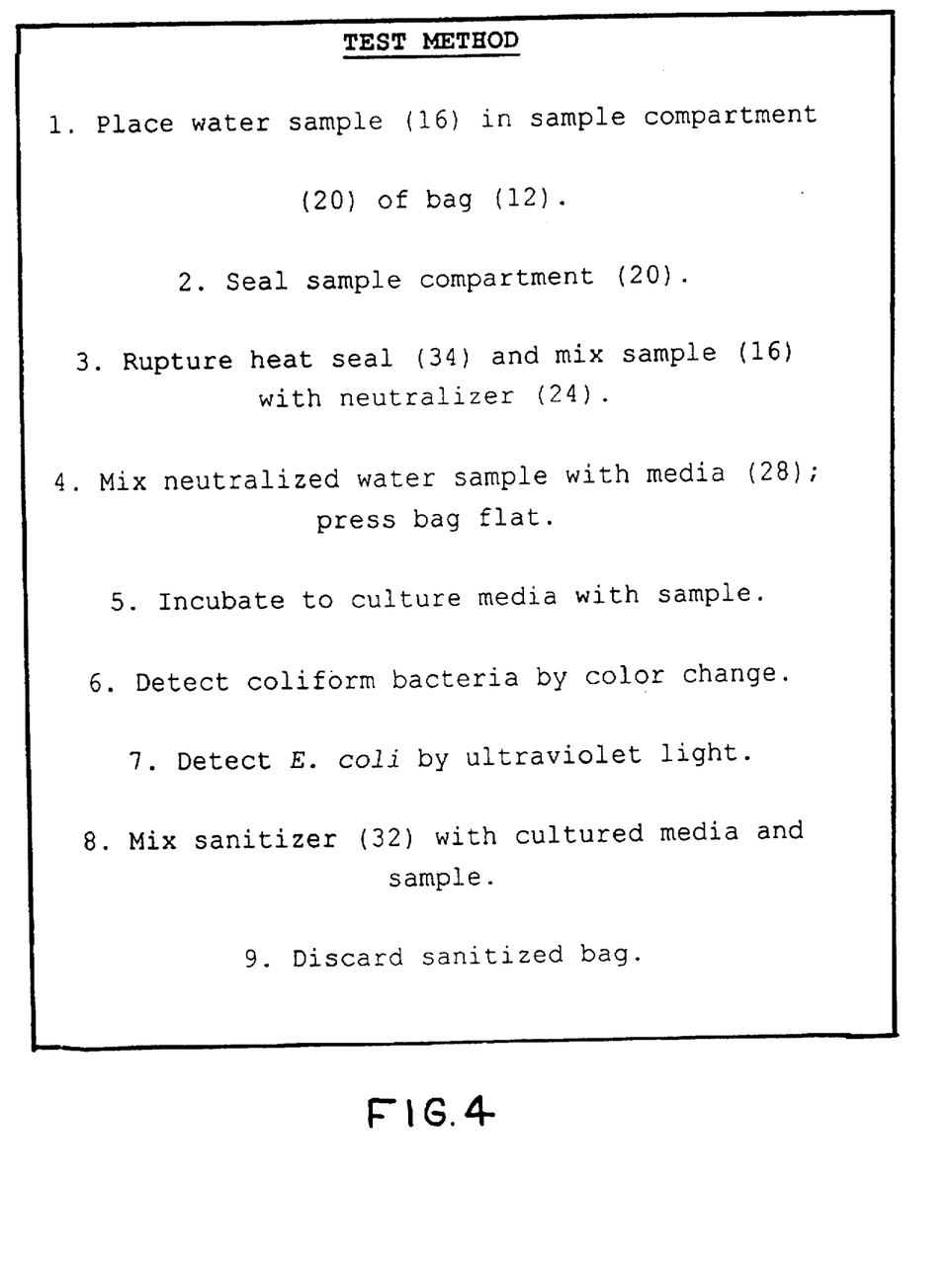
FIG. 4 is a sequence of method steps in the use of the test kit apparatus of the invention.

FIG. 4 shows a schematic diagram of the method of the invention, with the process steps shown and described.

Figure 5:
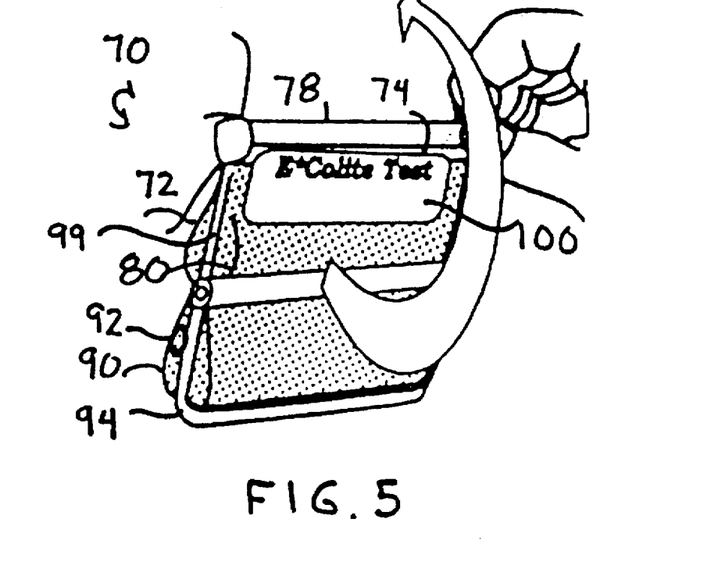
FIG. 5 is a perspective, illustrative view of another embodiment of the test kit apparatus of the invention.

FIG. 5 shows a perspective, illustrative view of another embodiment of the invention 70. The media bag 72 has an open top 74 to permit the entry of a water sample 76 directly into a media/indicator compartment 80. A closing wire 78 extends across the top of the open top 74 of the compartment 80. A removable plastic clip 94 separates the compartment 80 from the sanitizer compartment 90, which has a sanitizer in capsule form 92 sealed therein. An outer heat seal 99 extends around the three sides of the media bag 72 to seal all compartments of the media bag 72. An indicator grid 100 is printed on the top surface of the media and indicator compartment 80 to provide for reading of the mixed media sample 112. It is recognized that other printing or informative indicia may be printed on the media bag as required and desired.

Figure 6:
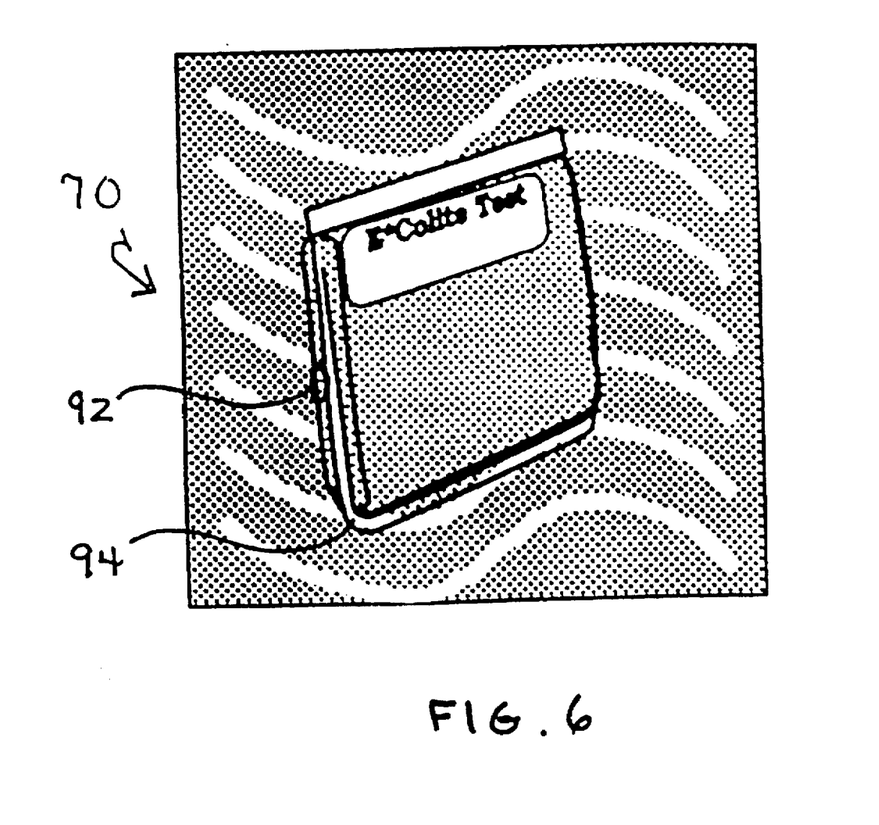
FIG. 6 is a perspective, illustrative view of the test kit apparatus of FIG. 4 in position for diagnosis.

FIG. 6 shows the test kit 70 in use, in a folded over, flattened position to enable incubation and subsequent reading of the incubated sample. The sanitizer capsule 92 is shown separated from the test sample by plastic clip 94.

Figure 7:
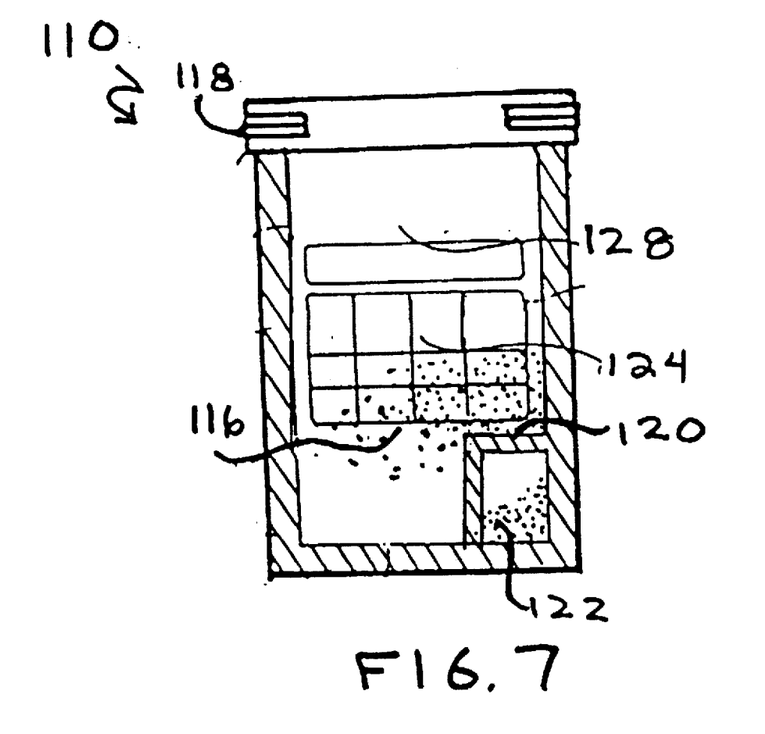
FIG. 7 is a perspective, illustrative view of another embodiment of the test kit apparatus of the invention.

FIG. 7 shows a further embodiment of the invention 100, with a time-release plug 120 containing sanitizer 122 in the single compartment 128. The sample to be tested 116 is placed directly into the main compartment 128 which compartment contains the media/indicator 114. The compartment is shown sealed by a tie seal means 118 and with print indicia 124 thereon.

In use, the water sample 16 to be tested is introduced into the open top 14 of the first sample compartment 20. The compartment is sealed by the user holding the two ends of the closing wire 18 and twirling the bag two or three times to create a tight foldover 42, with the user then forming a tie seal 44 with the closing wire 18. The test sample is then admixed with the neutralizer in the second compartment 24 after the removal of the rupturable heat seal 34 between the first 20 and second 22 compartments. Next, this admixture of the sample 16 and neutralizer 24 is admixed with the medium and indicator 28 in the third media/indicator compartment 26, after the removal of the rupturable heat seal 36 between the second 22 and third 26 compartments. This admixture of the neutralized test sample 16, 24 and medium 28 is then incubated, typically with the bag pressed in a flat condition.

After incubation, the admixture is evaluated by means of the indicia grid 40 to detect qualitatively and/or quantitatively the pathogens in the test sample. Prior to disposal, and typically after incubation and reading of the test sample, the used, incubated culture media with the test sample and the grown pathogens thereon is subsequently admixed with the sanitizer 32 of the fourth compartment 30 by the removal of the rupturable heat seal means 38 between the third 26 and fourth 30 compartments wherein the admixture of the sanitizer 32 destroys or renders inactive the growth pathogens and thereby permits the safe disposal of the entire packaging means or sealed plastic bag into the trash. The test kit and method are particularly adapted for test kits and apparatus used in the field and used by unsophisticated laboratory personnel or by consumers, and thus avoids the necessity of heat treating the sealed plastic bag or autoclaving the bag prior to removal of the dangerous components therein.

What is claimed is:

1. A safe, disposable test kit for the detection of pathogens in a test sample, which kit comprises:

a transparent, flexible, plastic bag packaging means to retain a test sample and of defined internal volume, which packaging means comprises a plurality of at least first and second separate, adjacent, sealed compartments, the packaging means having i) an opening at one end to permit a user to introduce a test sample into the first, sample, compartment, ii) a sealing means to seal the first compartment after introduction of the test sample, and iii) a divider means dividing the bag into the first, sample, compartment and the second, media, compartment and permitting a user to remove the divider means between the first and second compartments for admixing of the ingredients in the said compartments;

wherein the first sample compartment is adapted to receive therein a defined volume of a test sample to be tested for pathogens; and wherein the second media compartment contains a growth medium and a pathogen indicator to provide for growth on incubation of the pathogens and detection of the pathogens to be determined in the test sample; and sanitizing means to provide for the destruction of the pathogens after incubation and determination of the pathogens in the test sample, thereby permitting the destruction of the pathogens after growth in the incubated medium and the safe disposal of the packaging means.

2. The test kit of claim 1 wherein the sanitizing means comprises a separate pressure-rupturable capsule.

3. The test kit of claim 1 wherein the sanitizing means includes a dye indicator to indicate the full admixture of the sanitizing means with the incubated growth medium and the grown pathogens.

4. The test kit of claim 1 wherein the packaging means comprises a separate sealed third sanitizing compartment containing the sanitizing means.

5. The test kit of claim 4 wherein the sanitizing compartment is adjacent the media compartment and contains a pretimed plug to be dissolved by the test sample, so as to provide for the timed introduction of the sanitizing agent from the sanitizing compartment into the incubated cultured growth medium and the grown pathogens in the first and second compartments.

6. The test kit of claim 1 which includes a pressure-sensitive means to release the sanitizing means, the pressure-sensitive means containing the sanitizer means and adapted to be released into the first and second compartments after incubation by hand pressure applied by a user.

7. The test kit of claim 1 wherein said packaging means includes a third separate, sealed compartment adjacent to the first and second compartments and sealed therefrom, the third compartment containing a sanitizer composition as the sanitizing means to destroy the incubated pathogens on removal of the divider means between the sanitizing compartment and the other compartments by the user, thereby providing for the safe disposal of the packaging means after use.

8. The test kit of claim 1 wherein the divider means dividing the first and second compartments from each other comprises a removable plastic divider clip against the exterior surface of the plastic bag packaging means to provide for separate, adjacent, sealed compartments.

9. The test kit of claim 1 wherein the divider means comprises a heat seal line extending across the flexible plastic bag packaging means to provide for separate, adjacent, sealed first and second compartments, wherein the seal line may be overcome by the user to permit the admixture of ingredients between said compartments.

10. The test kit of claim 1 wherein the growth medium comprises a powdered composition having a growth nutrient medium for coliform bacteria and E. coli and having a first agent which is cleaved by an enzyme in coliform bacteria in the test sample to produce a color change, and a second agent which is cleaved by an enzyme in E. coli to produce a fluorescent color.

11. The test kit of claim 10 wherein the powdered composition also includes a water soluble, powdered gelling agent to provide for in situ gelling of the medium in the presence of water.

12. The test kit of claim 1 wherein the plastic bag packaging means contains on the surface thereof a means to aid in the quantitative detection of pathogens by a user after incubation.

13. The test kit of claim 1 wherein the growth medium is a powdered growth medium and includes a water soluble gelling agent to provide for the gelling of the medium upon admixing with a water or a water-containing test sample.

14. A safe, disposable test kit for the detection of pathogens in a test sample, which test kit comprises:

a transparent, flexible, multicompartment, plastic bag packaging means to receive a test sample, said packaging means having defined internal volume and comprising a plurality of at least first, second and third separate, adjacent, sealed compartments said packaging means having i) a first sample compartment which is open to receive therein a test sample to be tested for pathogens, ii) means to seal the open end of the sample compartment after receipt of the test sample, iii) removable seal means to seal the first and second compartments and the second and third compartments from each other and to permit a user to remove the seal means for the sequential mixing of the ingredients in the respective separate, sealed compartments, iv) a second media compartment containing a powdered growth nutrient medium and an indicator for the growth and detection of the pathogens to be detected, and v) a third sanitizing compartment containing a sanitizing composition to provide for the destruction of the pathogens after incubation, growth, and detection, thereby permitting the safe disposal of the packaging means.

15. The test kit of claim 14 wherein the packaging means further comprises a fourth sealed compartment between the first and second compartments, the fourth compartment containing therein a neutralizing agent to neutralize halogen in a water test sample.

16. The test kit of claim 14 wherein the removable seal means comprises a hand pressure rupturable sealing line extending across the plastic bag packaging means to provide separate first, second and third compartments.

17. The test kit of claim 14 wherein the removable seal means comprises a plastic divider clip against an exterior surface of the plastic bag packaging means to provide a seal line.

18. The test kit of claim 14 which includes a grid means on the surface of the compartments to permit the quantitative determination of the cultured pathogens.

19. The test kit of claim 14 wherein the plastic bag packaging means is an elongated, generally rectangular transparent, flexible plastic bag, comprising sealed compartments longitudinally aligned, and further wherein the seal means comprise generally parallel transverse heat-sealing lines.

20. The test kit of claim 14 wherein the third compartment contains an indicator which permits the user to have visual indication that the sanitizing composition has admixed fully with the grown pathogens to insure destruction of the pathogens.

21. The test kit of claim 20 wherein the indicator comprises a black, water soluble dye admixed with the sanitizing composition.

22. The test kit of claim 14 wherein the plastic bag packaging means comprises a multilayer plastic film material sealed about the peripheral edges.

23. The test kit of claim 14 wherein the sanitizing composition is selected to provide for the destruction of coliform bacteria and *E. coli*.

24. The test kit of claim 14 wherein the sanitizing composition is selected from the group consisting of: water soluble hypohalides; organic acids; peroxides; aldehydes; quaternary ammonium compounds; halogens; sulfates and combinations thereof.

25. The test kit of claim 24 wherein the sanitizing composition comprises a quaternary ammonium halide.

26. The test kit of claim 14 wherein the powdered medium comprises a first agent that provides for a visible color change as an indicator for the detection of coliform bacteria and a second agent that provides for the detection of *E. coli* by fluorescence.

27. The test kit of claim 26 further comprising an incubation means to incubate the packaging means at an incubation time and temperature sufficient to grow any pathogens present in a test sample, and an ultraviolet light source means to provide for the detection of *E. coli* through the employment of a fluorescent agent.

28. The test kit of claim 14 wherein the plastic bag packaging means is adapted to receive a water test sample having a volume of about 10 ml to 500 ml.

29. A test method for determination of pathogens in a test sample, which method comprises:
   a) introducing a test sample into a sample compartment in a transparent plastic bag packaging means and sealing the test sample within the sample compartment;
   b) providing a medium in a separate, sealed media compartment in the plastic bag packaging means, the media compartment containing a growth medium for the growth of the pathogens to be detected in the test sample and having an indicator agent therein to provide for detection of pathogens in the test sample;
   c) removing the seal between the test sample compartment and the media compartment and admixing the medium with the test sample;
   d) incubating the test sample in the medium in the sample and media compartments;
   e) observing and detecting the pathogens in the incubated test sample within the plastic bag packaging means;
   f) providing a sanitizing composition;
   g) introducing the sanitizing composition into the incubated sample and media compartments to provide for the total destruction of the pathogens grown in the compartments during incubation; and
   h) disposing of the plastic bag packaging means.

30. The method of claim 29 wherein said test sample is a water test sample to be tested for coliform bacteria and/or *E. coli* and said media compartment further contains a gelling agent, which gelling agent, on admixing with the water test sample, provides a gelled growth medium; and wherein said method comprises pressing the plastic bag packaging means with the gelled growth medium generally flat prior to the incubating of step d), and further wherein the observing and detecting of step e) comprises observing a change in color in the incubated gelled growth medium and quantitatively detecting coliform bacteria and/or *E. coli*.

31. The method of claim 30 wherein introducing the sanitizing composition comprises introducing said sanitizing composition from a separate sealed sanitizing compartment in the plastic bag packaging means into the media compartment by removing the seal between the sanitizing compartment and the media compartment.

32. The method of claim 31 wherein the sanitizing composition comprises a visible, water soluble dye indicator to indicate the admixture of the sanitizing composition with the incubated growth medium.

33. The method of claim 31 wherein the sample compartment, media compartment and sanitizing compartment are sealed from each other by removable clips, and which method includes removing the clips between compartments to provide for the admixing of the test sample, growth medium and sanitizing composition.

34. The method of claim 30 wherein the plastic bag packaging means includes a plurality of separate transversely sealed sequential compartments to include:
   a) a test sample compartment;
   b) a neutralizing compartment containing a neutralizing agent to neutralize halogens in the water test sample;
   c) a media compartment;
   d) a sanitizing compartment; and which method includes sequentially introducing the water test sample into the neutralizing compartment, the media compartment, and the sanitizing composition compartment.

35. The method of claim 30 wherein said observing and detecting includes employing a grid on the surface of the plastic bag packaging means to aid in the quantitative detection of the coliform bacteria or *E. coli*.

36. A disposable test kit for the detection of pathogens in a water test sample, which test kit comprises:
   a) a transparent, flexible, generally rectangular, plastic bag having a one and other end;
   b) a plurality of spaced-apart, generally parallel, heat-sealed, hand-rupturable dividing lines from the one to the other end, to form sequentially:
      i) a first water test sample compartment of selected volume to receive a water test sample therein;
      ii) a second media compartment, which includes powdered medium composition with a growth medium for the growth of the pathogens to be detected, a gelling agent which gels in the presence of the water test sample, and at least one agent which changes color in the presence of the pathogens to be detected; and
      iii) a third sanitizing compartment, which includes therein a sanitizing composition, selected to sanitize the pathogens grown on incubation of the medium composition and test sample, and to permit safe disposal of the bag after test completion;
   c) means to seal the one end of the bag after introduction of the water test sample into the first compartment; and
   d) means on the surface of the bag to provide for the estimated determination of the amount of the pathogens to be detected;
   whereby the water test sample is mixed with the media composition to provide a gelled growth composition, the gelled composition pressed generally flat in the bag, the bag with the flat gelled growth composition incubated, the presence of pathogens detected, and the bag sanitized by the introduction of the sanitizer composition into the bag.

37. The test kit of claim 36 wherein the sanitizing composition comprises a liquid quaternary ammonium composition.

38. The test kit of claim 36 wherein the apparatus is for the determination of a first pathogen and *E. coli*, and wherein the medium composition includes a first agent for the detection of the first pathogen and a second agent for the detection of *E. coli* by fluorescence.

39. The test kit of claim 36 for the detection of coliform bacteria and *E. coli*, wherein the medium composition comprises a first agent which is cleaved by an enzyme in coliform bacteria to produce a visible color change, and a second agent which is cleaved by an enzyme in *E. coli* to produce a fluorescence color.

* * * * *